US012285391B1

(12) United States Patent
McCarthy et al.

(10) Patent No.: US 12,285,391 B1
(45) Date of Patent: Apr. 29, 2025

(54) SYSTEM AND METHOD FOR NON-SURGICAL TREATMENT OF PROLAPSED HEMORRHOIDS

(71) Applicant: TCB Flash, LLC, Largo, FL (US)

(72) Inventors: Gloria McCarthy, Largo, FL (US); Michael McCarthy, Largo, FL (US)

(*) Notice: Subject to any disclaimer, the term of this patent is extended or adjusted under 35 U.S.C. 154(b) by 0 days.

(21) Appl. No.: 18/429,785

(22) Filed: Feb. 1, 2024

(51) Int. Cl.
| | |
|---|---|
| *A61K 31/137* | (2006.01) |
| *A61K 9/00* | (2006.01) |
| *A61K 31/167* | (2006.01) |
| *A61K 31/245* | (2006.01) |
| *A61K 31/4174* | (2006.01) |
| *A61K 31/4453* | (2006.01) |
| *A61K 31/47* | (2006.01) |
| *A61K 31/5375* | (2006.01) |
| *A61K 47/02* | (2006.01) |
| *A61K 47/36* | (2006.01) |
| *B08B 3/08* | (2006.01) |

(52) U.S. Cl.
CPC .......... *A61K 31/137* (2013.01); *A61K 9/0031* (2013.01); *A61K 31/167* (2013.01); *A61K 31/245* (2013.01); *A61K 31/4174* (2013.01); *A61K 31/4453* (2013.01); *A61K 31/47* (2013.01); *A61K 31/5375* (2013.01); *A61K 47/02* (2013.01); *A61K 47/36* (2013.01); *B08B 3/08* (2013.01)

(58) Field of Classification Search
CPC ...... B08B 3/08; A61K 31/137; A61K 9/0031; A61K 31/167; A61K 31/245; A61K 31/4174; A61K 31/4453; A61K 31/47; A61K 31/5375; A61K 47/02; A61K 47/36

See application file for complete search history.

(56) References Cited

U.S. PATENT DOCUMENTS

2005/0192210 A1* 9/2005 Rothbard ............... A61K 38/04
514/1.5

FOREIGN PATENT DOCUMENTS

WO    WO-0143735 A1 *  6/2001  ............. A61K 31/04

OTHER PUBLICATIONS

Ahad et al., Herbal Treatment for Hemorrhoids, JITPS, 2010, 1(5), pp. 236-244), and Leo et al. (Technical Tips and Tricks of Outpatients Treatments for Hemorrhoids, Haemorrhoids, 2018, pp. 151-166 (Year: 2018).*

Leo et al., Technical Tips and Tricks of Outpatients Treatments for Hemorrhoids, Haemorrhoids, 2018, pp. 151-166 (Year: 2018).*

* cited by examiner

*Primary Examiner* — Savitha M Rao
*Assistant Examiner* — Andrew P Lee
(74) *Attorney, Agent, or Firm* — Distinct Patent Law; Justin P. Miller

(57) ABSTRACT

The present invention provides a non-surgical method for treating prolapsed hemorrhoids. The first step is to clean the anus and surrounding areas, preferably with soap and warm water. The second step is to apply a powder that increases friction and dries the surface of the hemorrhoid. The third step is to gently push the prolapsed hemorrhoid back through the anal sphincter. After reinsertion, the drying effect of the powder prevents the hemorrhoid from prolapsing again by sufficiently increasing the friction to prevent passage through the anus. Held internally, the hemorrhoid shrinks, increasing user comfort.

17 Claims, 5 Drawing Sheets

SYSTEM AND METHOD FOR NON-SURGICAL TREATMENT OF PROLAPSED HEMORRHOIDS

FIELD

This invention relates to the field of hemorrhoids and more particularly to a system and method for treating hemorrhoids without surgery.

BACKGROUND

Hemorrhoids are vascular cushions found in the anal canal. Though present in everyone, they become problematic when inflamed, clotted, or prolapsed through the anus.

Straining during bowel movements can increase pressure in the rectum, enlarging the hemorrhoids. This swelling results from impaired venous drainage coupled with uninterrupted arterial blood flow. Aging weakens the connective tissues anchoring hemorrhoids in place, allowing them to protrude more readily. While part of typical anatomy, swollen or prolapsed hemorrhoids can cause discomfort.

Hemorrhoids are very common, especially among older adults. An estimated 13 million Americans have hemorrhoids, with 1.5 million new cases each year. They peak in prevalence between ages 45-65. Despite this, only about one-third of adults with hemorrhoids seek medical care. This may stem from embarrassment about discussing hemorrhoids, believing no good treatments exist, or facing a complicated referral process.

When a doctor's advice is sought, the hemorrhoids are graded on a 4-point severity scale. Grade 1 is for internal hemorrhoids that bleed but do not prolapse. Grade 2 hemorrhoids bleed and prolapse from straining but retract on their own. Grade 3 hemorrhoids bleed and prolapse. Grade 4 hemorrhoids remain permanently prolapsed outside the anus.

No single hemorrhoid treatment currently balances high effectiveness with low post-procedural pain and complications. Minimally-invasive options like rubber band ligation have few complications but work poorly long-term for significant hemorrhoids. More aggressive surgeries like hemorrhoidectomy and stapled hemorrhoidopexy remove hemorrhoids, but are painful with risks of complications.

An unmet need exists for a treatment that reliably and lastingly resolves moderate to severe (Grade 2-4) hemorrhoids, yet avoids severe pain and complications.

What is needed is a therapy that combines proven efficacy with gentle, non-invasive techniques to minimize recovery time and recurrence. Developing such an approach would meaningfully improve the care and quality of life for millions suffering from troublesome hemorrhoids.

SUMMARY

The present invention provides a non-surgical method for treating prolapsed hemorrhoids. A prolapsed hemorrhoid is an internal hemorrhoid that has grown sufficiently large to pass through the anus, and is therefore exposed externally. The hemorrhoid protrudes downward and stretches the membrane lining the anal canal. Prolapsed hemorrhoids appear as a pink/purple bulge protruding from the anus. They are covered with sensitive mucus membrane and may bleed or become irritated easily.

Internal hemorrhoids remain inside the anus and are not visible externally.

The first step is to clean the anus and surrounding areas, preferably with soap and warm water. The cleaning removes body oils, feces, mucous, and any other contaminants that may prevent the hemorrhoid from being held within the anus. Alternatives to soap and water include disposable wipes, the wipe including a soap or detergent to allow the oils and mucous to dissolve in water and be carried away.

The second step is to apply a powder that increases friction and dries or absorbs water from the surface of the hemorrhoid. The friction-increasing powder is also referred to as a drying or desiccating powder, or a friction-increasing powder. Preferred powders include talcum powder, corn starch, arrowroot starch, rice starch, oat flour, and baking soda. The powder optionally includes medications, such as vasoconstrictors, such as epinephrine, phenylephrine, and/or oxymetazoline, to narrow blood vessels to aid in the reduction of swelling. Other optional medications added to the powder include topical anesthetics, such as benzocaine, dibucaine, pramoxine, dyclonine, and/or lidocaine or similar.

The third step is to gently push the prolapsed hemorrhoid back through the anus. This can be done manually using a finger, or by using a tool designed for pushing on, manipulating, and handling hemorrhoids.

After reinsertion, the drying effect of the powder prevents the hemorrhoid from prolapsing again, or exiting the anus, by sufficiently increasing the friction to prevent passage through the anus. Restated, the hemorrhoid is held inside the body while it is allowed to shrink.

Held internally, after time the hemorrhoid shrinks, increasing user comfort.

Passing a stool may cause the hemorrhoid to again prolapse, requiring the treatment to be repeated.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
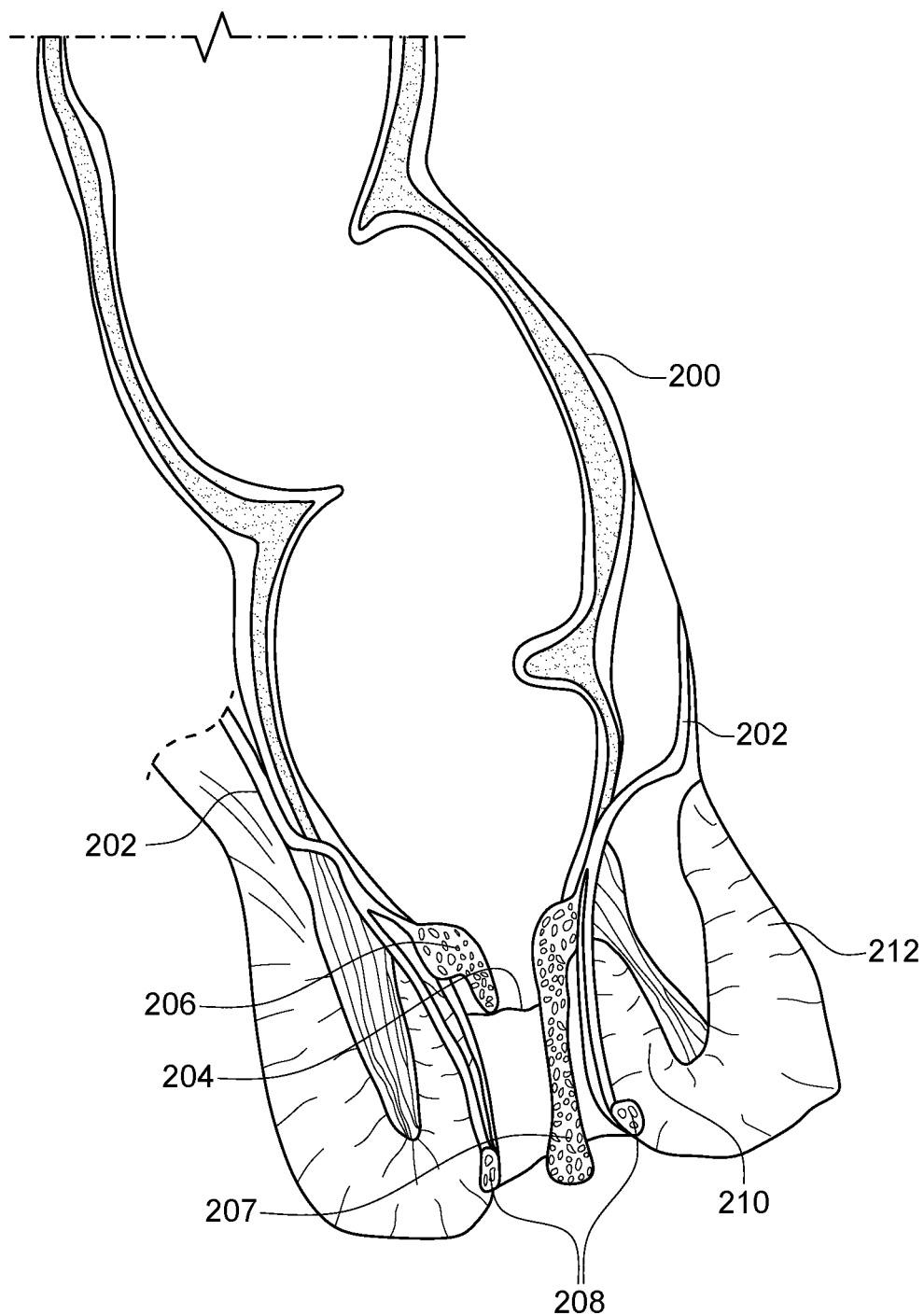
FIG. 1 illustrates a first view of a cross-sectional side view of the anus and rectum, with prolapsed hemorrhoid.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a first view of a cross-sectional side view of the anus and rectum, with prolapsed hemorrhoid, is shown.

The rectum 200 is shown, including the hemorrhoidal artery 202, dentate line 204, internal anal sphincter 210, and external anal sphincter 212.

Also shown are the internal hemorrhoid 206, prolapsed hemorrhoid 207, and external hemorrhoid 208.

The disclosed methodology is for treatment of the prolapsed hemorrhoid 207.

Figure 2:
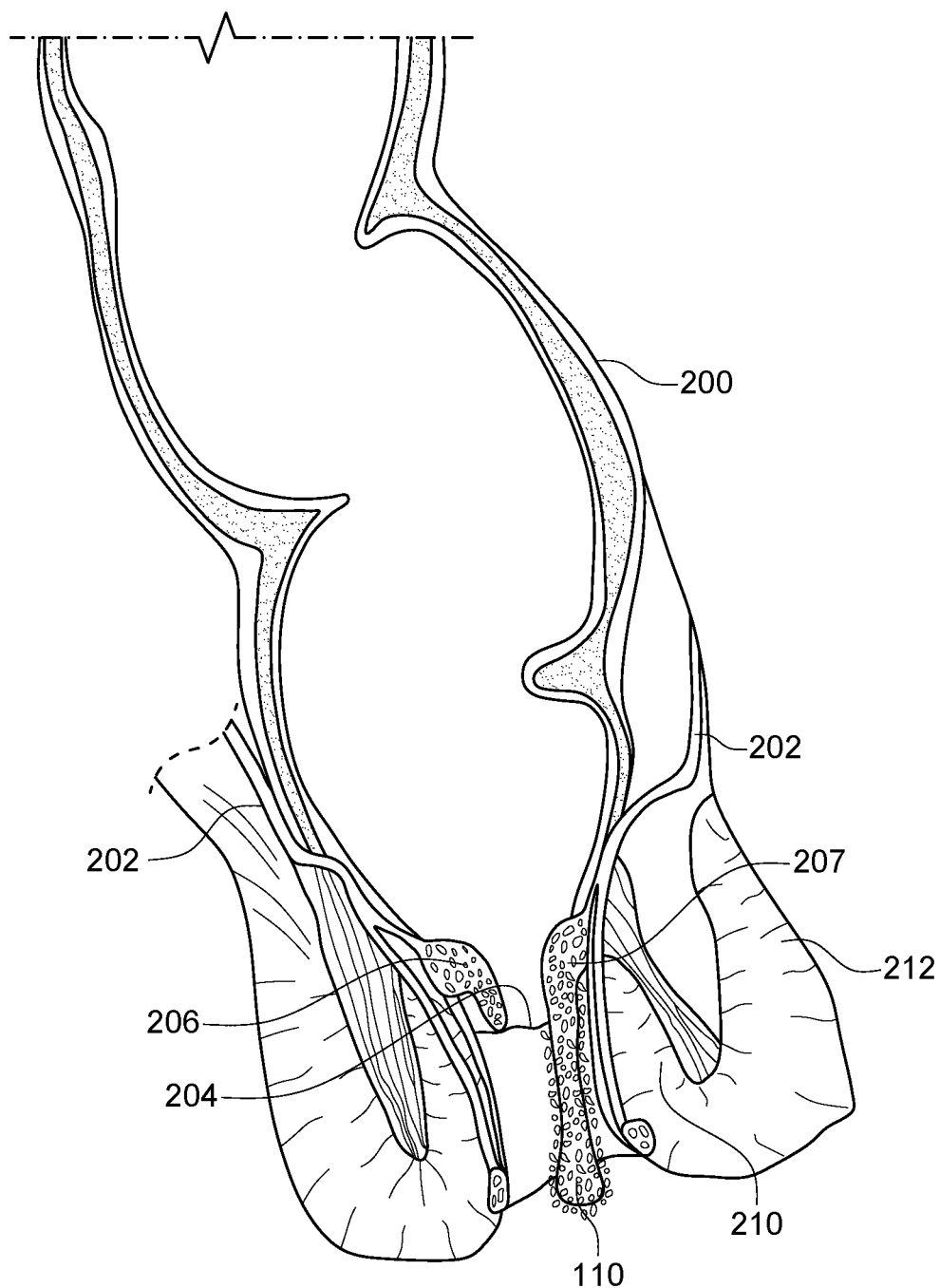
FIG. 2 illustrates a second view of a cross-sectional side view of the anus and rectum, with a prolapsed hemorrhoid coated in powder.

Referring to FIG. 2, a second view of a cross-sectional side view of the anus and rectum, with prolapsed hemorrhoid coated in powder, is shown.

The prolapsed hemorrhoid 207 is now coated in the drying and friction-increasing powder 110, ready to be pushed back into the body.

Figure 3:
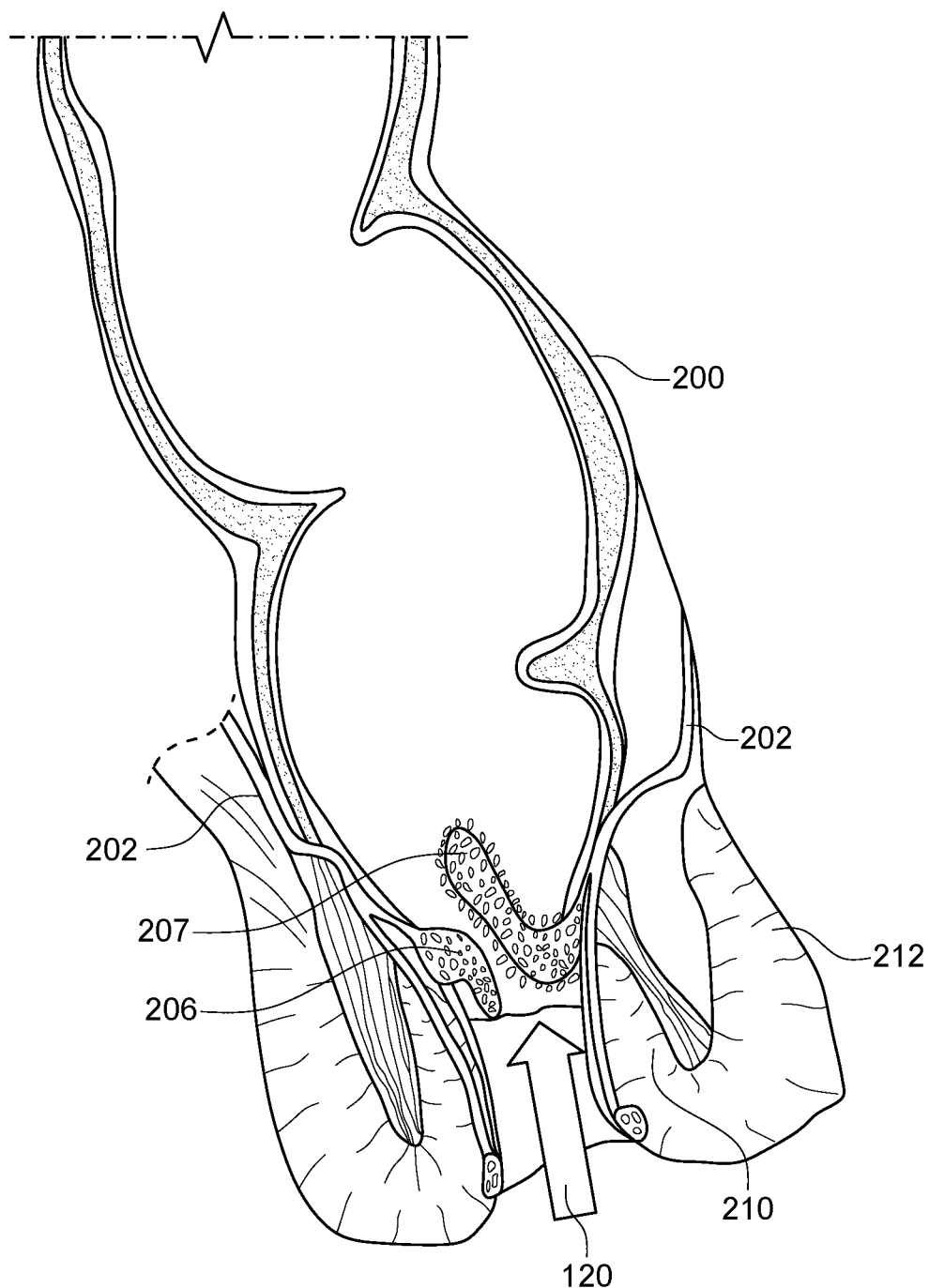
FIG. 3 illustrates a third view of a cross-sectional side view of the anus and rectum, with the prolapsed hemorrhoid coated in powder and pushed into the rectum.

Referring to FIG. 3, a third view of a cross-sectional side view of the anus and rectum, with prolapsed hemorrhoid coated in powder and pushed into the rectum, is shown.

By application of an insertion force 120, the prolapsed hemorrhoid 207 is pushed past the internal anal sphincter 210 and external anal sphincter 212.

Figure 4:
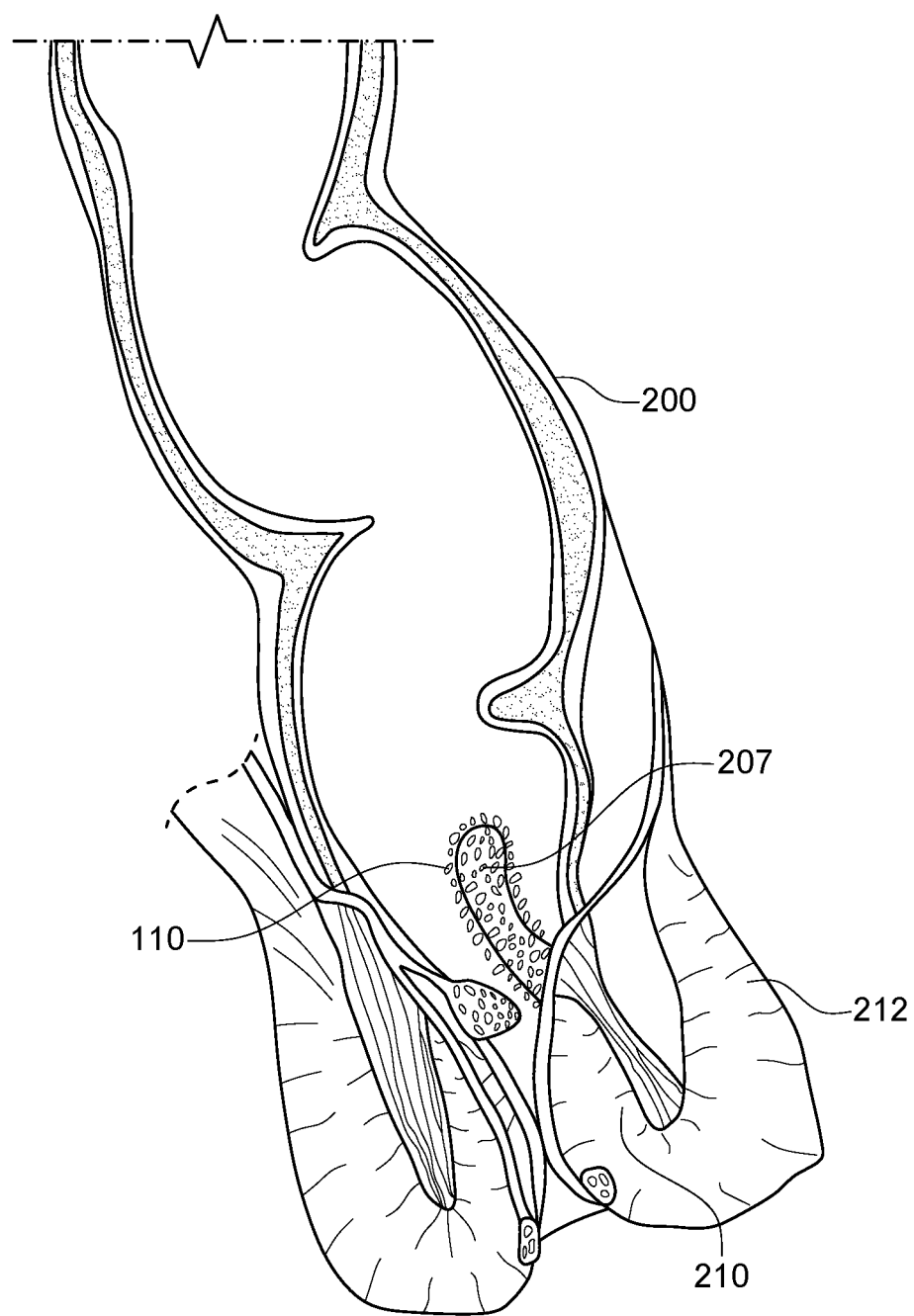
FIG. 4 illustrates a fourth view of a cross-sectional side view of the anus and rectum, with the prolapsed hemorrhoid shrinking.

Referring to FIG. 4, a fourth view of a cross-sectional side view of the anus and rectum, with prolapsed hemorrhoid shrinking, is shown.

Through natural construction of the internal anal sphincter 210 and external anal sphincter 212, in combination with the drying and friction-increasing powder 110, the prolapsed hemorrhoid 207 is held inside, where it can shrink.

Figure 5:
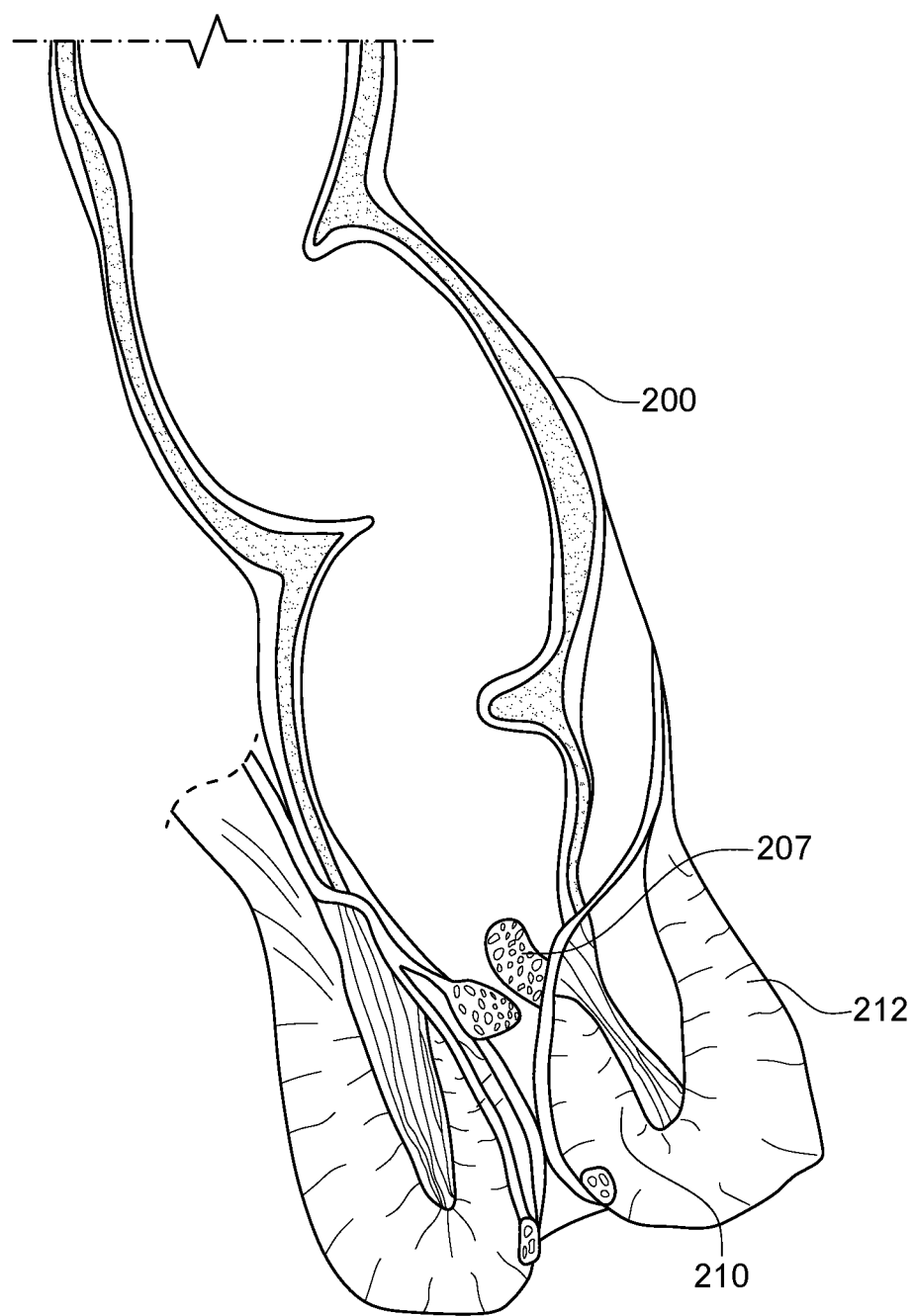
FIG. 5 illustrates a fifth view of a cross-sectional side view of the anus and rectum, with the prolapsed hemorrhoid shrunk.

Referring to FIG. 5, a fifth view of a cross-sectional side view of the anus and rectum, with prolapsed hemorrhoid shrunk, is shown.

Given sufficient time, the prolapsed hemorrhoid 207 has now shrunk, improving the users comfort.

Equivalent elements can be substituted for the ones set forth above such that they perform in substantially the same manner in substantially the same way for achieving substantially the same result.

What is claimed is:

1. A method for treating prolapsed hemorrhoids comprising:
    cleaning an anus and surrounding areas with soap and water to remove oils and mucous;
    applying a friction-increasing powder to a prolapsed hemorrhoid to dry a surface of the prolapsed hemorrhoid to increase friction;
    pushing the prolapsed hemorrhoid with friction-increasing powder through an anus;
        increased friction from the friction-increasing powder preventing the prolapsed hemorrhoid from passing back through the anus; and
    allowing the prolapsed hemorrhoid to shrink, increasing user comfort.

2. The method of claim 1, wherein the friction-increasing powder comprises talcum powder.

3. The method of claim 1, wherein the friction-increasing powder comprises corn starch.

4. The method of claim 1, wherein pushing the prolapsed hemorrhoid through the anus comprises manually pushing with a finger.

5. The method of claim 1, wherein the friction-increasing powder further comprises an anesthetic.

6. The method of claim 1, wherein the friction-increasing powder prevents the prolapsed hemorrhoid from exiting through the anus.

7. The method of claim 1, wherein the method provides non-surgical treatment of the prolapsed hemorrhoid.

8. A method for treating a prolapsed hemorrhoid, comprising the steps of:
    clean a prolapsed hemorrhoid using soap and water to remove oil and contaminants from a surface of the prolapsed hemorrhoid;
    apply a friction-increasing powder to a prolapsed hemorrhoid;
    push the prolapsed hemorrhoid through an external anal sphincter; and
    the friction-increasing powder holding the prolapsed hemorrhoid in place within the external anal sphincter, thereby causing the prolapsed hemorrhoid to shrink.

9. The method of claim 8, wherein the friction-increasing powder is a powder that causes drying, absorbing any water on the surface of the prolapsed hemorrhoid, thereby increasing friction.

10. The method of claim 8, wherein the friction-increasing powder comprises talcum powder.

11. The method of claim 8, wherein the friction-increasing powder further comprises a vasoconstrictor.

12. The method of claim 11, wherein the vasoconstrictor is selected from the group consisting of epinephrine, phenylephrine, oxymetazoline, and combinations thereof.

13. The method of claim 8, wherein the friction-increasing powder further comprises a topical anesthetic.

14. The method of claim 13, wherein the topical anesthetic is selected from the group consisting of lidocaine, benzocaine, dibucaine, pramoxine, dyclonine, and combinations thereof.

15. The method of claim 8, wherein the step of pushing the prolapsed hemorrhoid through the external anal sphincter utilizes a finger or a medical tool designed for hemorrhoid manipulation.

16. The method of claim 8, wherein the prolapsed hemorrhoid is held in place for a time sufficient to allow shrinking and relief of symptoms.

17. A method for treating a prolapsed hemorrhoid, comprising:
    cleaning an anus and prolapsed hemorrhoid with soap and water;
    applying a friction-increasing powder consisting of talcum powder, corn starch, arrowroot starch, rice starch, oat flour, baking soda, or combinations thereof to the prolapsed hemorrhoid;
    pushing the friction-increasing-powder-coated prolapsed hemorrhoid through an anal sphincter using a finger or hemorrhoid manipulation tool;
        increased friction provided by the friction-increasing powder holding the prolapsed hemorrhoid within the anal sphincter;
    maintaining the prolapsed hemorrhoid in an internal position for a time sufficient to allow shrinking of the prolapsed hemorrhoid, thereby providing relief from hemorrhoid symptoms.

* * * * *